(12) United States Patent
Kindlein et al.

(10) Patent No.: US 8,301,228 B2
(45) Date of Patent: Oct. 30, 2012

(54) REAL TIME RADIATION TREATMENT PLANNING SYSTEM

(75) Inventors: Johann Kindlein, Oberhausen (DE); Dimos Baltas, Darmstadt (DE); Georgios Sakas, Darmstadt (DE); Frans Kuipers, Veenendaal (NL); Hans Martin Schot, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 0 days.

(21) Appl. No.: 13/013,051

(22) Filed: Jan. 25, 2011

(65) Prior Publication Data

US 2011/0288361 A1 Nov. 24, 2011

Related U.S. Application Data

(63) Continuation of application No. 10/448,311, filed on May 30, 2003, now Pat. No. 7,899,517.

(30) Foreign Application Priority Data

Jun. 17, 2002 (EP) .................................... 02077436

(51) Int. Cl.
*A61B 6/00* (2006.01)
(52) U.S. Cl. ........ 600/436; 600/407; 600/424; 600/427; 600/443; 601/2; 601/3
(58) Field of Classification Search .................. 600/407, 600/427, 439, 443, 436, 424; 601/2, 3
See application file for complete search history.

(56) References Cited

U.S. PATENT DOCUMENTS

| | | | |
|---|---|---|---|
| 5,391,139 A | 2/1995 | Edmundson | |
| 5,868,757 A | 2/1999 | Koutrouveli | |
| 5,931,786 A | 8/1999 | Whitmore, III et al. | |
| 6,095,975 A | 8/2000 | Silvern | |
| 6,200,255 B1 | 3/2001 | Yu | |
| 6,273,858 B1 * | 8/2001 | Fox et al. | ........................ 600/466 |
| 6,360,116 B1 * | 3/2002 | Jackson et al. | ................ 600/427 |

(Continued)

OTHER PUBLICATIONS

Ghanei A. et al., *Medical Physics*, Oct. 2001, AIP for American Assoc. Phys. Med, USA, vol. 28, No. 10, pp. 2147-2153.

(Continued)

*Primary Examiner* — Brian Casler
*Assistant Examiner* — Joel Lamprecht
(74) *Attorney, Agent, or Firm* — Finnegan, Henderson, Farabow, Garrett & Dunner LLP

(57) ABSTRACT

The invention relates to a real time radiation treatment planning system for use in effecting radiation therapy of a preselected anatomical portion of an animal body using hollow needles. According to embodiments of the invention, the system may include a processing means processing means-configured to perform a three-dimensional imaging algorithm and a three-dimensional image segmentation algorithm, with respect to one or more specific organs within the pre-selected anatomical portion and with respect to the needles, for converting the image data obtained with an imaging means into a three-dimensional image of the anatomical portion, using at least one single or multi-objective anatomy-based genetic optimization algorithm. For pre-planning or virtual simulation purposes, the processing means is arranged to determine in real time the optimal number and position of at least one of the needles, positions of energy emitting sources within the needles, and the dwell times of the energy emitting sources at the positions. For post-planning purposes, the processing means is arranged to determine, based on three-dimensional image information, in real time the real needle positions and the dwell times of the energy emitting sources for the positions.

20 Claims, 8 Drawing Sheets

U.S. PATENT DOCUMENTS

| | | | |
|---|---|---|---|
| 6,387,034 | B1 | 5/2002 | Lee |
| 6,422,989 | B1 | 7/2002 | Hektner |
| 6,438,401 | B1 | 8/2002 | Cheng et al. |
| 6,514,191 | B1 | 2/2003 | Popowski et al. |
| 6,561,980 | B1 * | 5/2003 | Gheng et al. .......... 600/443 |
| 6,599,230 | B2 | 7/2003 | Hastings et al. |
| 6,610,013 | B1 * | 8/2003 | Fenster et al. .......... 600/439 |
| 7,022,062 | B1 | 4/2006 | Murphy |
| 7,041,048 | B2 | 5/2006 | Drobnik et al. |
| 7,171,255 | B2 * | 1/2007 | Holupka et al. .......... 600/427 |
| 2002/0038117 | A1 | 3/2002 | Tokita et al. |
| 2002/0091315 | A1 | 7/2002 | Spetz |
| 2003/0100814 | A1 | 5/2003 | Kindlein |
| 2003/0208119 | A1 | 11/2003 | Crowley |
| 2003/0233123 | A1 | 12/2003 | Kindlein et al. |

OTHER PUBLICATIONS

Yu, *Medical Physics*, Sep. 1997, AIP for American Assoc. Phys. Med, USA, vol. 24, No. 9, pp. 1445-1454.

Yu et al., Medical Physics, Dec. 1996, AIP for American Assoc. Phys. Med, USA, vol. 23, No. 12, pp. 2085-2091.

Lahanas et al., *Medical Physics*, Sep. 1999, AIP for American Assoc. Phys. Med, USA, vol. 26, No. 9, pp. 1904-1918.

Lahanas et al., *Evolutionary Multi-Criterion Optimization*. First International Conference, EMO 2001. Proceedings (Lecture Notes in Computer Science Vo. 1993), Evolutionary Multi-Criterion Optimization. First International Conference, EMO 2001, Zurich Switzerland, 7, pp. 574-587.

Milickovic et al., *Evolutionary Murti-Criterion Optimization*. First International Conference, EMO 2001. Proceedings (Lecture Notes in Computer Science Vo. 1993), Evolutionary Multi-Criterion Optimization. First International Conference, EMO 2001, Zurich Switzerland, 7, pp. 167-180.

Pathak et al., *Medical Imaging 1999*, Image Display, San Diego, CA, USA, Feb. 21-23, 1999, vol. 3658, pp. 2-8, XP008011149, Proceedings of the SPIE—The International Society for Optical Engineering, 1999, SPIE—Int. Soc. Opt. Eng, USA.

* cited by examiner

REAL TIME RADIATION TREATMENT PLANNING SYSTEM

This application is a continuation application of U.S. application Ser. No. 10/448,311, entitled REAL TIME RADIATION TREATMENT PLANNING SYSTEM, filed May 30, 2003, now U.S. Pat. No. 7,899,517 of Johann KINDLEIN et al., currently pending, which claims the right of priority under 35 U.S.C. §119 to European Application No. 02077436.0 filed on Jun. 17, 2002, the entire disclosures of which are fully incorporated herein by reference.

BACKGROUND

The invention relates to a real time radiation treatment planning system for use in effecting radiation therapy of a pre-selected anatomical portion of an animal body, comprising:

A a stepper for automatically positioning imaging means for generating image data corresponding to the anatomical portion;

B means for inserting under the guidance of a template at least one hollow needle at a position into said anatomical portion;

C radiation delivery means for defining a plurality of positions having a spatial relationship within a volume of said anatomical portion and for inserting at least one energy emitting source through said at least one hollow needle at said plurality of positions into said anatomical portion;

D processing means for generating a radiation treatment plan for effecting said radiation therapy, said treatment plan including information concerning:

the number, position, direction and estimation of the best way of placement of one or more of said hollow needles within the anatomical portion and volume of said anatomical portion to be treated;

the amount of radiation dose to be emitted.

The last decade has seen major changes in the way radiation treatments are delivered. The century-old objective of radiation therapy, i.e. to deliver a curative dose to the target, e.g. a tumour, while preserving normal tissues of the animal body can now be aimed at with a high degree of sophistication. However, despite of major improvements achieved with three-dimensional imaging techniques, that allow the anatomy to be properly defined, brachytherapy treatments have not yet fully benefited from these important new pieces of information.

For brachytherapy using high dose rate (HDR) energy emitting sources, catheters or hollow needles are placed in a target volume within an animal body and it is assumed that if the dose distribution covers the catheters, it should also cover the anatomy. Imaging is commonly used to set the treatment margins, but optimized dose distributions are based on considerations, such as the catheter positions and desired dose and limited to a few defined points. This necessarily results in an approximation of the shape of the anatomical portion to be treated.

For the case of treatments of the prostate, volume optimization results in a dose distribution that is essentially cylindrically shaped. With a cylindrically shaped approximation of the prostate it is possible to assure the complete coverage of the prostate volume with the radiation emitted by the source or sources. Only a conformal dose distribution delivered to the anatomical portion with an adequate margin around the prostate will encompass all affected, cancerous tissue.

The methods described in the prior art (e.g. Etienne Lessard, Med. Phys. 28. (5), May 2001) are using the concept of inverse planning to obtain an anatomy-based optimization of the dose distribution. Without any manual modification to deliver conformal HDR prostate treatment and knowing the exact location of the applicators (catheters/hollow needles), due to modern imaging techniques, it is easy to determine the possible stopping position of the radioactive source within a catheter or hollow needle present in the animal body. The possible source positions are considered given. The system has to determine based on a HDR inverse planning dose optimization governed entirely from anatomy and clinical criteria to decide the best dwell time distribution.

In U.S. Pat. No. 5,391,139 in the name of G. K. Edmundson a real time radiation treatment planning system according to the preamble is disclosed. With this system image data of the anatomical portion, e.g. the prostate is obtained for planning purposes and the medical personnel chooses an arbitrary number of needle locations using predetermined placement rules, which have been empirically determined from experience. The planning system develops a treatment plan based on these arbitrary needle positions after which the medical personnel has to examine the planning results and decide whether these results are suitable for the performing the actual radiation treatment. In case the medical personnel finds the planning results unsatisfactorily the virtual needle positions have to be altered and using the repositioned needles a new treatment plan is generated. This trial-and-error approach is repeated until a treatment plan is developed that satisfies the actual intended radiation treatment.

Subsequently the catheters or needles are inserted via a template into the animal body according to the generated treatment plan.

Conventional dose optimization algorithms are single objective, i.e. they provide a single solution. This solution is found by a trial-and-error search method as in Edmundson's U.S. Pat. No. 5,391,139, by modifying importance factors of a weighted sum of objectives, e.g. by repositioning the virtual needles or by changing the radiation dose to be delivered. This problem has been addressed currently and some methods have been proposed to find an optimal set of importance factors.

Conventional optimization methods combine the target objectives and the objectives for the surrounding healthy tissue and of critical structures into a single weighted objective function. The weight or importance factor for each objective must be supplied. The obtained solution depends on the value of importance factors used. One goal of a treatment planning system is the ability to assist the clinician in obtaining good plans on the fly. Also it should provide all the information of the possibilities given the objectives of the treatment. In order to explore the feasible region of the solution space with respect to each objective, different values for the importance factors in the aggregate objective function must be given.

Furthermore, the appropriate values of these importance factors differ from clinical case to clinical case. This implies that for any new clinical case a lot of effort is necessary for their determination.

While current optimization methods are single weighted objective methods the dose optimization problem is a true multi-objective problem and therefore multi-objective optimization methods should be used.

The gradient-based algorithm due to its efficiency allows the construction of the so-called Pareto or trade-off surface which contains all the information of the competition between the objectives which is necessary for the planner to select the solution which best fulfills his requirements.

One problem of this algorithm is that the weighted sum as used in all conventional dose optimization algorithms cannot provide solutions in possible non-convex parts of the Pareto tradeoff surface, because a convex weighted sum of objectives converges only to the convex parts of the Pareto front. Another major limitation of the algorithm is its restriction to convex objective functions for which gradients can be calculated. In this case according to the Kuhn-Tucker theorems a global optimum can be obtained and the entire Pareto front is accessible from the weighted sum.

When searching for an optimal set of importance factors dividing each importance factors in n points, then the number of combinations for k objectives is approximately proportional to $n^{k-1}$ and the shape of the entire trade-off surface require a very large computational time. Most realistic problems require the simultaneous optimization of many objectives. It is unlikely that all objectives are optimal for a single set of parameters. If this is so, then there exist many, in principle infinite solutions.

A multi-objective algorithm does not provide a single solution, but a representative set of all possible solutions. Out of these representative solutions a single final solution has to be selected. It is a complex problem to automatically select such a solution and such methods have been proposed but then a planner would not know what alternatives solutions could instead be selected. In problems where different sets of objectives have to be compared this information is valuable, since it shows the possibilities a planner has for each such set.

A time analysis of the optimization with available commercial systems based on e.g. 35 clinical cases shows that even if a single optimization run requires only a few seconds the actual optimization requires 5.7±4.8 minutes. The evaluation of the results requires additional 5.8±2.5 minutes. This shows that the result of a single optimization run is not always satisfactorily and most of the time is spent in a manual trial-and-error optimization.

The invention aims to obviate the above described problems and proposes a new real time radiation treatment planning system according to the above preamble, where the possible positions of the energy emitting sources are not considered given and the location of the needles are not pre-determined based on rules, which have been empirically determined.

It is also an object of the present invention to describe a new real time radiation treatment planning system and method, which will allow a significant speed-up of single and multi-objective anatomy based dose optimization and inverse planning procedures for HDR interstitial brachytherapy.

More in particular the invention aims to generate in real time a treatment plan, which will be presented to the medical personnel instantly and can also immediately used as the radiation treatment.

BRIEF DESCRIPTION OF THE DRAWINGS

FIG. 16 shows a first exemplary view of a "show results of all solutions" dialog;

FIG. 17 shows a second exemplary of the "show results of all solutions" dialog;

DETAILED DESCRIPTION

Figure 1:
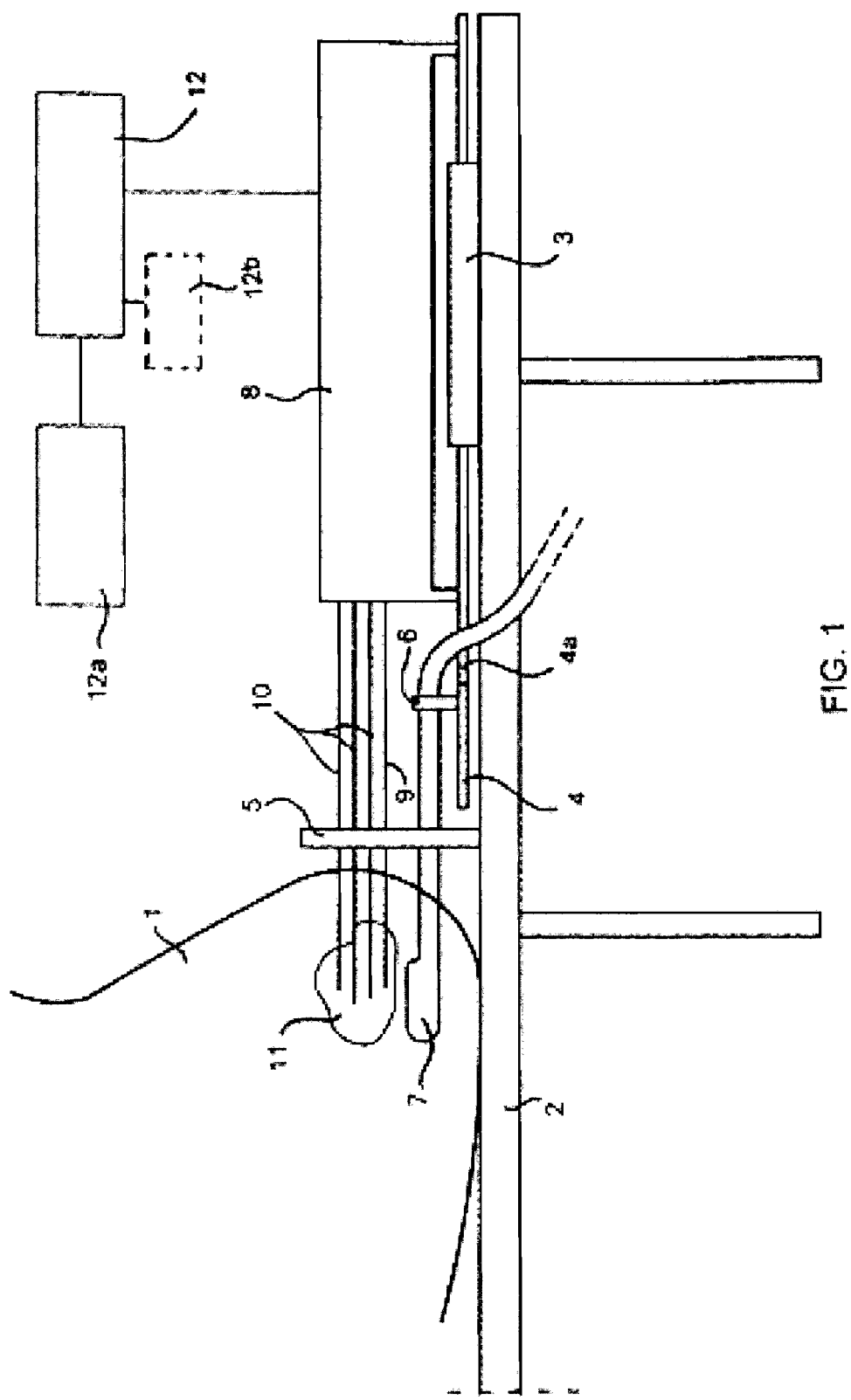
FIG. 1 shows a schematic of an exemplary device for implanting an energy emitting source.

According to the invention said processing means are provided with a three-dimensional imaging algorithm and a three-dimensional image segmentation algorithm for at least the specific organs within said anatomical portion and the needles for converting the image data obtained with said imaging means into a three-dimensional image of the anatomical portion, whereby by using at least one single or multi-objective anatomy based genetic optimization algorithm for pre-planning or virtual simulation purposes said processing means are arranged to determine in real time the optimal number and position of at least one of said hollow needles, the position of said energy emitting source within each hollow needle as well as the dwell times of said energy emitting source at each position; whereas for post planning purposes said processing means are arranged to determine based on three-dimensional image information in real time the real needle positions and the dwell times of said energy emitting source for each position.

The term needles in this application also covers e.g. catheters, guide tubes or other elements to be implanted in an animal body for positioning an energy emitting source inside that animal body. The three-dimensional image segmentation algorithm used in the treatment planning system according to the invention may use all or part of these elements (hollow needles, catheters, and guide tubes, e.g.).

The use of a three-dimensional imaging algorithm and a three-dimensional image segmentation algorithm allows a real time and fast generation of a treatment plan without the necessity of determining certain objectives as a starting point for the treatment planning step, such as the positioning of one or more needle inside the anatomical portion.

In fact with the treatment planning system according to the invention for generating a treatment plan said anatomy based genetic optimization algorithm uses specific animal body related data and/or system related data and/or radiation related data, wherein said animal body related data are data concerning the shape and localization of said anatomical portion and/or the shape and localization of specific organs near or within said anatomical portion.

Said system related data may be data concerning the template and its position in relation to said anatomical portion of said animal body and/or the dimensions of the needles used and/or the minimum displacement distance of said energy emitting source through said radiation delivery means, whereas said radiation related data are data concerning the prescribed radiation dose to said anatomical portion of said animal body, the maximum radiation exposure dose to said specific organs near or within said anatomical portion.

These specific data are used as boundary conditions and entered into the anatomy based genetic optimization algorithm by the medical personnel or determined/established by said algorithm from e.g. said image data obtained with the imaging means.

Dose optimization has to consider many objectives in conflict, such as the coverage of the pre-selected anatomical portion or planning target volume (PTV) to be treated with a specified dose and the dose protection of the surrounding tissue and specific delicate organs (OAR=organs at risk), such as the bladder and urethra, when treating prostate cancer. The objectives are combined into a single objective function $f_{Tot}$ formed by a weighted sum of the individual objective functions. The optimal value f*i for the $i^{th}$ objective found by a optimization algorithm depends on the weights (importance factors) used and may not be the best possible result as the mapping from importance to objective space is complex, especially for three and more objectives. In cases where the solution is not satisfactory the treatment planner is required to repeat the optimization with a different set of importance factors. One method is to increase the importance factors of the objectives for which the solution does not provide a satisfactory result.

Practical only a very small number of combinations can be tested and with this approach the treatment planner cannot gain all the information about the range of possible values and the degree of competition, which are required to select the "best solution". In order to get the "best" possible result avoiding trial-and-error methods the invention proposes and uses a gradient based multi-objective optimization algorithm.

The importance of this has been recognized by the U.S. Pat. No. 6,327,490, where a method is presented to save and compare different treatment plans. What is not recognized in this patent is that not only a modification of the energy emitting source positions is sometimes necessary, but also a modification of the importance factors/boundary conditions, which determine the quality of the solution. In clinical practice the reality is often that the optimization required is multi-objective rather than single-objective and this increases even further the time required for the calculation process. Consequently there is a real need in anatomy based optimization techniques and inverse planning procedures for very fast dose calculation methods.

The dose $d_i(X)$ at the $i^{th}$ sampling point is calculated by:

$$d_i(x) = \sum_{j=1}^{N_d} x_j^2 \tilde{d}_{ij}$$

where $N_d$ is the number of sources, $x_j^2$ is the dwell time of the $j^{th}$ source dwell position and $\tilde{d}_{ij}$ the kernel value for the $i^{th}$ dose calculation point and $j^{th}$ source dwell position. Dose calculation look-up tables (LUT) of $\tilde{d}_{ij}$ are calculated and stored in a preprocessing step. The calculation of the dose for $N_s$ sampling points requires $N_s N_d$ multiplications and $N_s(N_d-1)$ additions.

A Fast Fourier Transform (FFT) based convolution technique for the calculation of a three-dimensional dose distribution has been proposed by Boyer and Mok in 1986, which tries to reduce the calculation time. Employing FFT based convolution methods the time needed for the calculation of a dose distribution with this method is independent of the number of sources. While unable to cope with angular asymmetric kernels, an advantage of the FFT based method is that the computational time is practically independent of the form of the dosimetric kernel used. Our analysis has shown that this method is comparable with conventional methods only if the number of sources is much larger than 300. The avoidance of wrap around effects can only be avoided with zero padding in each dimension which increases the transform size to $N=8.N_s$ for $N_s$ sampling points and requires $8.N_s.\ln(8.N_s)$ operations.

The aim of HDR brachytherapy dose optimization according to the invention is to cover the anatomical portion (PTV) to be treated with at least some dose value, and to protect the specific delicate organs (OAR) and the surrounding normal tissue with dose values above some specific level. For variance based objective functions dose values above a critical dose value are penalized quadratic. The objectives are such that the isodose of the optimal dose distribution of the prescription dose coincides with the surface of the anatomical portion. With this approach, the use of an additional objective for the surrounding normal tissue is not necessary. For this the dose variance $f_s$ of the sampling points (dose points) as uniformly distributed on the surface of the anatomical portion should be as small as possible. The avoidance of excessive high dose values inside the anatomical portion, e.g. the prostate is controlled by the dose distribution variance $f_v$ inside the anatomical portion.

Normalized variances are used:

$$f_s = \frac{1}{N_s} \sum_{i=1}^{N_s} \frac{(d_i^s - m_s)^2}{m_s^2}, \quad f_v = \frac{1}{N_v} \sum_{i=1}^{N_v} \frac{(d_i^v - m_v)^2}{m_v^2}$$

where $m_s$ and $m_v$ are the average dose values on the surface of the anatomical portion and within the anatomical portion respectively, and $N_s$, $N_v$ the corresponding numbers of sampling points. The objective space of ($f_s$, $f_v$) is convex and gradient-based algorithms converge to the global Pareto front. If specific, delicate organs are to be considered then an additional objective is included for each specific organ (OAR):

$$f_{OAR} = \frac{1}{N_{OAR}} \sum_{i=1}^{N_{OAR}} \frac{\Theta(d_i^{OAR} - D_c^{OAR} m_s)(d_i^{OAR} - D_c^{OAR} m_s)^2}{(D_c^{OAR} m_s)^2},$$

$$\Theta(x) = \begin{cases} 1 & x \geq 0 \\ 0 & x < 0 \end{cases}$$

where $N_{OAR}$ is the number of sampling points in the specific organ and $D_c^{OAR}$ is the corresponding critical dose as a fraction of the prescription dose or reference dose, which dose equals in this model the average dose on the surface of the anatomical portion. The objective functions for the specific delicate organs are of the same form as for the anatomical organs, but involve the dose variances versus the critical dose values, which are specific only to those particular specific organs. The derivatives are:

$$\frac{\partial f_s}{\partial x_k} = \frac{4x_k}{N_s m_s^3} \sum_{i=1}^{N_s} d_i^s (m_s \tilde{d}_{ik}^s - d_i^s \tilde{m}_k^s)$$

$$\frac{\partial f_v}{\partial x_k} = \frac{4x_k}{N_v m_v^3} \sum_{i=1}^{N_v} d_i^v (m_v \tilde{d}_{ik}^v - d_i^v \tilde{m}_k^v)$$

$$\frac{\partial f_{OAR}}{\partial x_k} = \frac{4x_k}{N_{OAR}(D_C^{OAR})^2 m_s^3}$$

$$\sum_{i=1}^{N_{OAR}} \Theta(d_i^{OAR} - D_c^{OAR} m_s)(d_i^{OAR} - D_c^{OAR} m_s)(m_s \tilde{d}_{ik}^{OAR} - d_i^{OAR} \tilde{m}_k^s)$$

Where the following relations are used:

$$d_i^s = \sum_{i=1}^{N_d} x_l^2 \tilde{d}_{il}^s, \, m_s = \frac{1}{N_s} \sum_{i=1}^{N_s} d_i^s, \, \tilde{m}_k^s = \frac{1}{N_s} \sum_{i=1}^{N_s} \tilde{d}_{ik}^s, k = 1, \ldots N_d$$

$$d_i^v = \sum_{i=1}^{N_d} x_l^2 \tilde{d}_{il}^v, \, m_v = \frac{1}{N_v} \sum_{i=1}^{N_v} d_i^v, \, \tilde{m}_k^v = \frac{1}{N_v} \sum_{i=1}^{N_v} \tilde{d}_{ik}^v, k = 1, \ldots N_d$$

$$d_i^{OAR} = \sum_{i=1}^{N_d} x_l^2 \tilde{d}_{il}^{OAR}$$

where $d_i^s$, $d_i^v$ and $d_i^{OAR}$ is the dose rate at the $i^{th}$ sampling point on the surface of the anatomical portion, within the anatomical portion and within a specific organ respectively. $\tilde{d}_{i_{il}}^S$, $\tilde{d}_{i_{il}}^V$, $\tilde{d}_{i_{il}}^{OAR}$ is the dose kernel for the $i^{th}$ sampling point and the $l^{th}$ source dwell position for the sampling points on the surface of the anatomical portion, within the anatomical portion and in the specific organ respectively. $N_d$ is the number of source dwell positions.

For a conventional method to calculate objective values and derivatives the lookup table $\tilde{d}_{i_{ia}}^S$ as a $N_s \times N_d$ matrix $\tilde{K}^S$ are considered:

$$K^s = \begin{pmatrix} \tilde{d}_{il}^s & \tilde{d}_{12}^s & \cdots & \tilde{d}_{1Nd}^s \\ \tilde{d}_{21}^s & \tilde{d}_{21}^s & \cdots & \tilde{d}_{2Nd}^s \\ \vdots & \vdots & \ddots & \vdots \\ \tilde{d}_{Nsl}^s & \tilde{d}_{Ns2}^s & \cdots & \tilde{d}_{NsNd}^s \end{pmatrix}$$

If $\vec{d}^{sT} = (d_1^s, d_2^s, \ldots, d_{Ns}^s)$ is the vector of dose values $d_i^s$ and $t^{-T} = (t_1, t_2, \ldots, t_{Nd}) = (x_1^2, x_2^2, \ldots, x_{Nd}^2)$ the vector of the dwell times, then $\vec{d}^s = \tilde{K}^s \vec{t}$.

The conventional approach is to calculate the dose values and then the objective values and their derivatives. The number of operations to calculate $\vec{d}^s$ requires $N_d \cdot N_s$ multiplications and $(N_d-1) \cdot N_s$ additions. The storage required for $\tilde{K}^S$ is $N_d \cdot N_s$ floating points. The storage of this pre-computed matrix is desired because of the significant gain in the optimization speed. The calculation of the objective functions and the derivatives for $N_s$ sampling points and $N_d$ source dwell positions requires therefore an order of $N_d \cdot N_s$ operations.

The New Method of the Calculation of the Objectives and Derivatives Using Dose Kernel Look-Up Tables The objective function $f_s$ and its $N_d$ derivatives can be written also as:

$$f_s = \left[\frac{1}{N_s m_s^2} \sum_{i=l}^{N_s} (d_1^s)^2\right] - 1, \, \frac{\partial f_s}{\partial x_k} = \frac{4x_k}{N_s m_s^2} \sum_{i=1}^{N_s} d_i^s \tilde{d}_{ik}^s + \frac{4x_k \tilde{m}_k^s}{N_s m_s^3} \sum_{i=1}^{N_s} (d_i^s)^2$$

$$k = 1, 2, \ldots, N_d$$

It is possible to reduce the number of operations of the objective value and its derivatives to approximately $O(N_d \cdot N_d)$ operations. With $\vec{d}^{sT} = \vec{t}^T \tilde{K}^{sT}$ we have $$\sum_{i=1}^{NS} (d_i^S)^2 = \vec{d}^{sT} \cdot \vec{d}^s = \vec{t}^T \tilde{K}^{sT} \tilde{K}^s \vec{t} = \vec{t}^T D^s \vec{t}.$$

$D^s$ is a symmetric ($D_{\alpha\beta}^S = D_{\beta\alpha}^S$) $N_d \times N_d$ matrix. We call $\tilde{K}^S$ the first order and $D^s$ the second order dose kernel matrix.

The terms $m_s$, $m_s^2$ and $$\sum_{i=1}^{N_S} d_i^S \tilde{d}_{i\beta}^S$$

can be calculated from $\tilde{K}^S$ using the relations:

$$m_S = \vec{s}^{sT} \tilde{K}^S \vec{t},$$

$$m_S^2 = \vec{t}^T \tilde{K}^{sT} \vec{s}\vec{s}^T \tilde{K}^S \vec{t} = \vec{t}^T \vec{\tilde{m}}^S \vec{\tilde{m}}^{sT} \vec{t},$$

$$\sum_{i=1}^{N_S} d_i^S \tilde{d}_{i\beta}^S = \left(\vec{s}^{sT} \tilde{K}^S\right)_\beta$$

where $$\vec{s}^{sT} = \frac{1}{N_S}(1, 1, 1, \ldots, 1)$$

is a $N_s$ dimensional vector and $\vec{\tilde{m}}^{sT} = \vec{s}^{sT} \tilde{K}^S$.

From the matrix representation the following terms can be written analytically as:

$$g_\alpha \equiv \sum_{i=1}^{N_S} d_i^S \tilde{d}_{i\alpha}^S = \sum_{\beta=1}^{N_d} x_\beta^2 D_{\alpha\beta}^S \quad (1)$$

$$\sum_{i=1}^{N_S} (d_i^s)^2 = \sum_{\alpha=1}^{N_d} \sum_{\beta=1}^{N_d} x_\alpha^2 x_\beta^2 D_{\alpha\beta}^S = \sum_{\alpha=1}^{N_d} x_\alpha^2 \sum_{\beta=1}^{N_d} x_\beta^2 D_{\alpha\beta}^S = \sum_{\alpha=1}^{N_d} x_\alpha^2 g_\alpha \quad (2)$$

$$m_S = \sum_{\alpha=1}^{N_d} x_\alpha^2 \tilde{m}_\alpha^S \quad (3)$$

where $$D_{\alpha\beta}^S = \sum_{i=1}^{N_S} \tilde{d}_{i\alpha}^S \tilde{d}_{i\beta}^S.$$

For the objective $f_v$ the corresponding matrices $\tilde{K}^V$ and $\tilde{D}^v$ are required. $D^v$ and $D^v$ can be calculated once in a preprocessing step which requires only 1-2 seconds.

The equations (1)-(3) show us that it is possible to increase the number of sampling points in the anatomical portion without increasing the optimization time as the right side of each equation does not directly depend on the number of sampling points. This means that we can increase accuracy without increasing the computation costs.

With the new approach the number of operations is independent on the number of sampling points. It is not necessary to store the matrix $\tilde{K}^S$ and $\tilde{K}^V$. Only the matrices $D^S$, $D^V$ and the $N_d$ dimensional vectors $\tilde{K}^{sT}\bar{s}^s$ and $\tilde{K}^{vT}\bar{s}^v$ are required for the dose optimization. The matrices $\tilde{K}^S$ and $\tilde{K}^V$ require $N_s \cdot N_d$ and $N_v \cdot N_d$ numbers to be stored, whereas both symmetric matrices $D^S$ and $D^V$ require $N_d(N_d+1)$ numbers to be stored, i.e. the storage is independent on the number of sampling points.

It is of importance to mention that this novel algorithm can be applied in general for objectives (and their derivatives) of the following types commonly used in brachytherapy (HDR and seeds) and external beam radiotherapy:

$$f_1 = \frac{1}{N}\sum_{i=1}^{N}(d_i - D_1)^2 \quad (4)$$

$$f_1 = \frac{1}{N}\sum_{i=1}^{N}d_i \quad (5)$$

$$f_3 = \frac{1}{N}\sum_{i=1}^{N}d_i^2 \quad (6)$$

where $D_i$ is the desired dose for the $i^{th}$ sampling point and N the number of sampling points. Objectives of the form $f_2$ and $f_3$ are used for the surrounding normal tissue, where the dose has to be minimized. $f_2$ is a measure of the integral dose, whereas with $f_3$ high dose values are penalized stronger than with $f_2$.

For external beam radiotherapy and intensity modulated beam radiotherapy (IMRT) due to the sparse matrix nature of the kernel matrix we have a benefit only if the sampling point density is such that the average number of sampling points per beamlet is larger than the number of beamlets.

Furthermore it is to mention that since the kernel of an inverse planning system is based on the calculation of anatomy related objective functions, it is obvious that the same benefit is expected when this novel method is implemented as described in the Equations 1 to 3 above.

In order to optimize for the specific organ's the objective function and the derivatives are build up only by terms for which $d_i^{OAR} > D_c^{OAR}m_S$, which is expressed by $\Theta(d_i^{OAR} - D_c^{OAR}m_S)$. A large fraction of the sampling points has dose values that are smaller than $D_c^{OAR}m_S$. It is possible to avoid the calculation of a fraction of these dose values using the Cauchy-Schwarz-Bunjakovski inequality:

$$\sum_{i=1}^{N_s} d_i b_i \leq \sqrt{\sum_{i=1}^{N} a_i^2} \sqrt{\sum_{i=1}^{N} b_i^2}$$

For the dose $d_i$ of the $i^{th}$ sampling point we have $$d_i \sum_{i=1}^{N_d} x_i^2 \tilde{d}_{il} \leq \sqrt{\sum_{i=1}^{N_d} x_i^4} \sqrt{\sum_{i=1}^{N_d} \tilde{d}_{il}^2}$$

The quantity $$r = \sqrt{\sum_{i=1}^{N_d} x_i^4}$$

is calculated only once in each iteration while the $N_s$ constants $$p_i = \sqrt{\sum_{i=1}^{N_d} \tilde{d}_{il}^2}, i = 1, \ldots, N_s$$

can be calculated and stored in a pre-processing step. If $r \cdot p_i < D_c^{OAR}m_s$ it follows $d_i < D_c^{OAR}m_s$, otherwise it is necessary to calculate $d_i$. Even if the estimation of the dose by the inequality is not very good it is possible to avoid the calculation of the dose values of a large fraction of the sampling points in the specific organs using only one multiplication per point.

A better estimate can be obtained using the relation:

$$d_i = \sum_{l=1}^{Nd} x_l^2 \tilde{d}_{il} \leq \sqrt{\sum_{l=1}^{Nd1} x_l^4} \sqrt{\sum_{l=1}^{Nd1} \tilde{d}_{il}^2} + \sqrt{\sum_{l=Nd1+1}^{Nd} x_l^4} \sqrt{\sum_{l=Nd1+1}^{Nd} \tilde{d}_{il}^2} \leq$$

$$\sqrt{\sum_{l=1}^{Nd} x_l^4} \sqrt{\sum_{l=1}^{Nd} \tilde{d}_{il}^2}, i = 1, \ldots, Ns$$

where $N_d$ is divided into 2 approximately equal terms $N_1$, $N_2$, i.e. $N_d = N_1 + N_2$.

The two terms $$\sqrt{\sum_{l=1}^{Nd1} x_l^4} \text{ and } \sqrt{\sum_{l=Nd1+1}^{Nd} x_l^4}$$

can be calculated in each iteration once while the $2N_s$ terms $$\sqrt{\sum_{l=1}^{Nd1} \tilde{d}_{il}^2} \text{ and } \sqrt{\sum_{l=Nd1+1}^{Nd} \tilde{d}_{il}^2}$$

are calculate once and stored in a pre processing step before the optimization.

This method can be extended to objective functions of the type $$f_H(x) = \frac{1}{N}\sum_{i=1}^{N} \Theta(d_i(x) - D_H)(d_i(x) - D_H)^a$$

For a=2 we obtain the quadratic type of objectives, for a=1 the Lessard-Pouliot objectives and for a=0 the DVH based objectives. Using the inequality we can avoid the calculation of the dose of a fraction of the sampling points if $r \cdot p_i < D_H$. For the rectum, bladder and normal tissue this approach avoids the calculation of a significant fraction of the dose values.

The main idea of the proposed dose optimization speed-up method is that the objective functions presented here and commonly used in brachytherapy and their derivatives can be calculated without the calculation of the individual dose values or a fraction of them. For objectives of the type given by equation (4)-(6) the number of operations for the calculation of the objective function values and their derivatives is independent of the number of sampling paints, if we ignore the pre processing time to calculate and store $\vec{s}^{s^T}\tilde{K}^S$ and $D^S = \vec{s}^{s^T}\tilde{K}^S$.

This method allows us to increase the number of sampling points in the anatomical portion up to a few thousands, improving thus the accuracy without any loss of optimization speed. In comparison to standard dose optimization the new method is faster the more sampling points we have. The speed-up is also significant for implants with a small number of source dwell positions, where the term $N_s^2$ is much smaller than $N_s \cdot N_d$ required previously for the calculation of the dose values.

A multi-objective optimization with 100 sources using up to 100 solutions and up to 5000 sampling points in the anatomical portion with a 2 GHz PC is possible in less than 10 s. The storage for $N_s$ sampling points and $N_d$ sources can be reduced by a factor of approximately $2N_s/N_d$.

A speed-up is expected not only for deterministic algorithms but also for stochastic algorithms such as genetic algorithms or simulated annealing.

For high dose limits objectives an estimation of the dose value using only two multiplications and one addition per sampling point avoids the necessity of the calculation of the dose value of a fraction of the sampling points.

FIG. 1 shows in very schematic form various elements of a known device for implanting an energy emitting source, e.g. radioactive seeds into a prostate gland. A patient 1 is shown lying in lithotomy position on a table 2. Fixedly connected to the table 2 is a housing 3. Housing 3 comprises a drive means 4 to move rod 4a stepwise. A template 5 is connected or mounted to the table 2, which template is provided (not shown) with a plurality of guiding holes through which holes hollow needles 9, 10 can be positioned relative to the patient. By means of a holder 6 a transrectal imaging probe 7 is fixedly connected to said rod 4a, which is moveable in a direction towards and from the patient by means of the drive means 4. The imaging probe 7 can be an ultrasound probe.

A needle 9 is used for fixing the prostate gland 11 in position relative to the template 5. A number of needles 10 is fixed into position through the template 5 in the prostate gland 11. The template 5 determines the relative positions of the needles 10 in two dimensions. The needles 10 are open at their distal ends and are sealed of by a plug of bio-compatible, preferably bio-absorbable wax. In said housing 3 a seed loading unit 8 is present.

A well-known therapy planning module 12a is provided for determining the number and relative positions of seeds in each needle for implantation in the prostate gland 11. Such therapy planning module 12a usually comprises a computer programmed with a therapy planning program. The therapy planning module 12a is connected to the seed loading unit 8 through a control device 12 for controlling the number of seeds for each needle. Control device 12 may be a separate device or may be an integrated part either of the seed 1 oading unit 8 or of the therapy planning module 12a or may be embodied in the software of the therapy planning module 12a or of the seed loading unit 8.

The known device shown in FIG. 1 operates as follows. A patient 1 is under spinal or general anesthesia and lies on the operating table 2 in lithotomy position. The (ultrasound) imaging probe 7 is introduced into the rectum and the probe is connected via signal line 7a with a well known image screen, where an image may be seen of the inside of the patient in particular of the prostate gland 11 as seen from the point of view of the imaging probe 7. The template 5 is attached to the drive means 4, thereby insuring the correlation of the ultrasound image geometry and the template 5. The prostate gland 11 is fixed relative to the template 5 and the drive means 4 and the imaging probe 7 by means of one or more needles 9, 10. Subsequently further needles 10 are introduced in the body and the prostate gland under ultrasound guidance one by one.

Moving the imaging probe with the drive means 4 longitudinally within the rectum controls the needle depths of each needle 10. After all needles 10 have been placed, their positions relative to the prostate gland 11 are determined in at least one of several known ways. In a known way the therapy planning module 12a determines how the needles 10 are to be placed in the prostate and how many radioactive seeds are to be placed in what order in each of the needles 10. The information about the desired placement of the radioactive seeds in the needles 10 is used to control the seed loading unit 8.

According to the invention said therapy treatment planning module generates at least one treatment plan as it is provided with a three-dimensional imaging algorithm and a three-dimensional image segmentation algorithm for the specific organs within said anatomical portion, the needles and the tubes for converting the image data obtained with said imaging means into a three-dimensional image of the anatomical portion, whereby by using at least one single or multi-objective anatomy based genetic optimization algorithm for pre-planning or virtual simulation purposes said processing means are arranged to determine in real time the optimal number and position of at least one of said hollow needles, the position of said energy emitting source within each hollow needle as well as the dwell times of said energy emitting source at each position; whereas for post planning purposes said processing means are arranged to determine based on three-dimensional image information in real time the real needle positions and the dwell times of said energy emitting source for each position.

Figure 2:
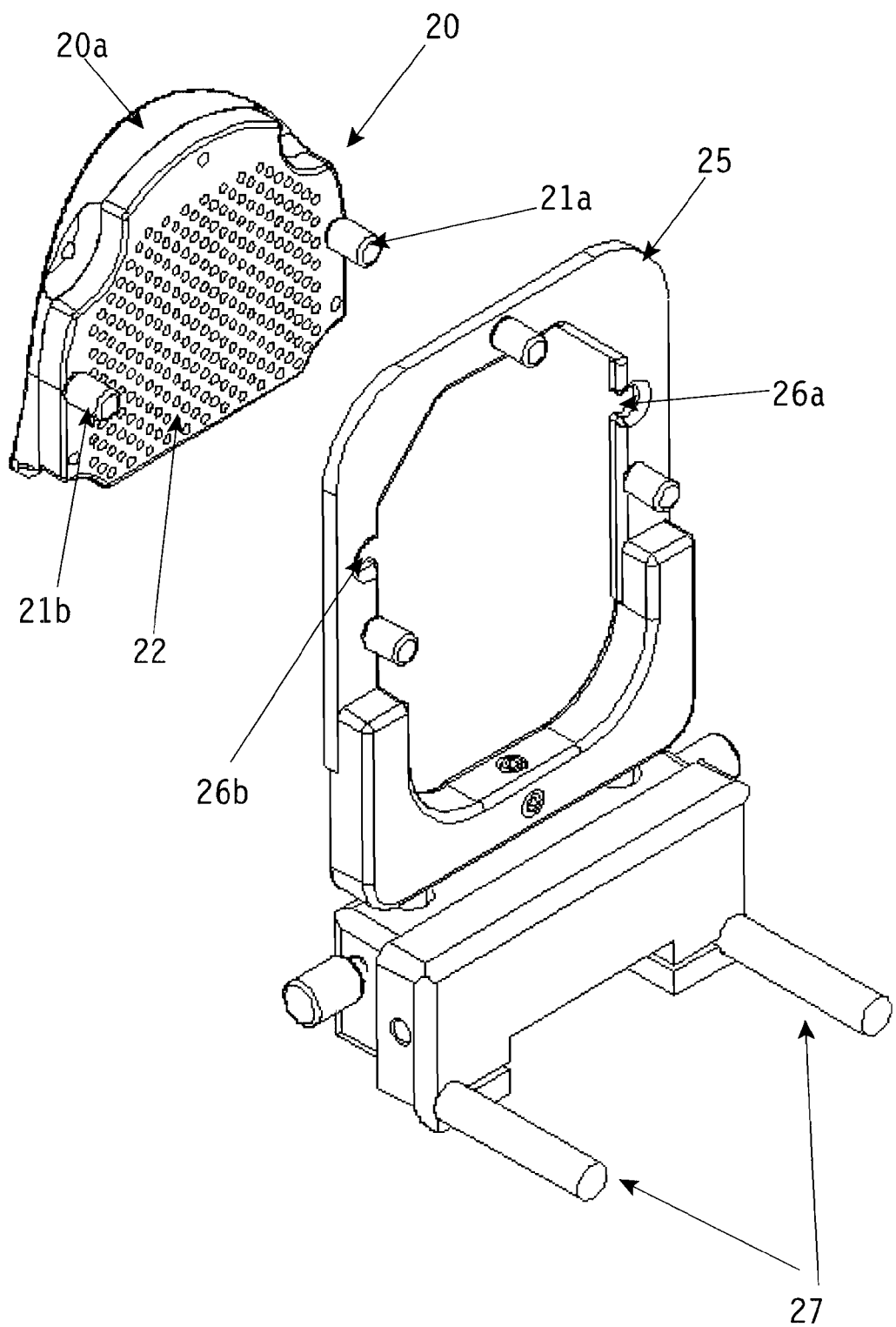
FIG. 2 shows an exemplary template for use in a real time radiation treatment planning system.

In FIG. 2 a template is disclosed for use in a real time radiation treatment planning system according to the invention. Especially the template 20 is detachable from a template frame 25, which frame is connected with the stepper means for displacing the imaging means as described in connection with FIG. 1.

According to the invention template 20 has a grid configuration with needle holes 22 at an intermediate distance of 3.5 mm seen in diagonal direction. In another embodiment the template has a grid configuration with needle holes at an intermediate distance of 2.5 mm seen in orthogonal direction.

In a specific embodiment the template is a motorized template without holes and the needles are guided with a guiding tube, whereas the guiding tube can be positioned in each position of the virtual template grid. As this embodiment does not use holes, the absence of a grid does not limit the positioning of the needles in relation to the template and the anatomical portion to be treated. In fact with a template without holes the grid configuration is only limited to the diameter of the needles used.

A more specific embodiment of the template is disclosed in FIG. 2, where said template 20 is detachable from the frame 25. Frame 25 is connected with the stepper means as described above. For a good connection and orientation of the frame 25 and template 20 in relation to the device of FIG. 1 the frame 25 is provided with alignment pins 27 which corporate with corresponding openings (not shown) in the device of FIG. 1.

The template 20 has a saddle shaped body 20a, which fits with the frame 25 as shown in FIG. 2. For alignment purposes the template 20 is provided with notches 11a-11b which cooperate with corresponding holes 26a-26b present in the circumference of frame 25.

It is an another object of the invention to describe the catheters or needles inserted in the body through which the HDR source is travelling with their real geometrical dimensions. As a direct result of this it is a next object of the invention that sampling points for dose evaluation, which are lying inside the needles or catheters are excluded. This will contribute to the reduction of the number of sampling points in the anatomical portion compared with other conventional methods and to the increase of the speed.

Figure 3:
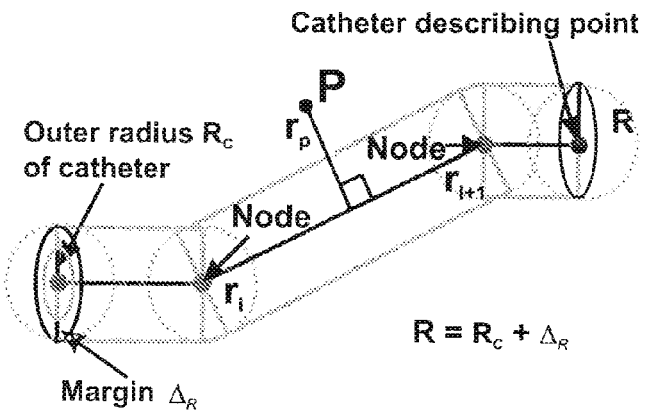
FIG. 3 shows an exemplary catheter or hollow needle.

As shown in FIG. 3 a catheter or hollow needle is defined by catheter describing points. These points are connected with cylinders and at each catheter describing lengths and diameters. The set of catheters cylinders and spheres are used to describe the geometry of a catheter that may be either metallic linear or plastic and curved.

For generating each treatment plan the processing means of the radiation treatment planning system according to the invention are arranged to generate a set of multiple sampling points using said three-dimensional imaging algorithm and said three-dimensional image segmentation algorithm and to calculate the optimal radiation dose distribution for each of said sampling points by using a gradient-based algorithm.

The quality of the results depends on the distribution of the sampling points as generated. According to the invention the dose distribution inside the anatomical portion (PTV), critical structures, such as specific delicate organs (OAR) and the surface of the anatomical portion is estimated from the dose of a small number of points (sampling points).

Figure 4:
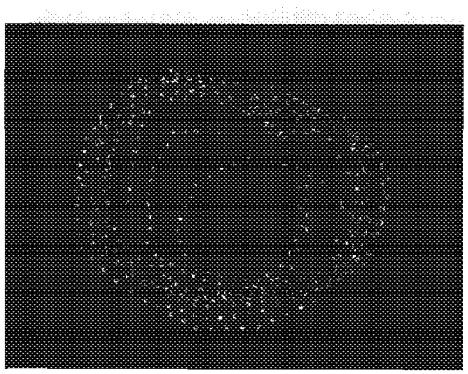
FIG. 4 shows exemplary generated sampling points distributed on the contours of the anatomical portion to be treated.
Figure 5:
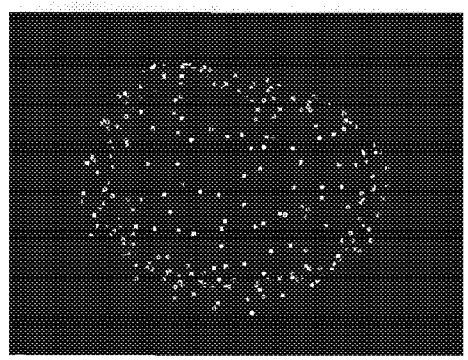
FIG. 5 shows exemplary generated sampling points distributed on the triangulated surface of the anatomical portion to be treated.

As shown in FIGS. 4 and 5 the generated sampling points are distributed on the contours and on the triangulated surface of the anatomical portion to be treated. For the contour based method no points are on both ends of the anatomical portion. Therefore a large part of the surface is undefined for the optimization algorithm and the resulting isodose is bounded only by the contours of the anatomical portion.

Sampling points in the volume are generated from low discrepancy sequences or quasi-random distributed sampling points.

It is a another objective of the invention that in contrast to pseudo-random distributed sampling points voids and clustering are avoided. Monte-Carlo generated quantities convergence much more rapidly than a conventional pseudo-random sequence. Sampling points inside catheters are excluded. This reduces the influence of very large dose values of sampling points that occasionally are produced very close to the source dwell positions. Statistical values obtained from the sampling points are calculated therefore with a higher accuracy.

According to the invention two treatment planning steps are performed:

Pre-Planning or Inverse Planning:
Given the geometry of the anatomical portion (PTV) to be treated, the specific organs (OAR) near or within said anatomical portion, a template and its position the optimal number and position of needles, the dwell positions and the dwell times of the energy emitting source are determined, so that the resulting dose distribution satisfies various criteria such as coverage of the anatomical portion with the prescription dose, avoidance of dose values above some critical values in the specific organs, etc.

Postplanning:
Given the geometry of the anatomical portion (PTV) and the specific organs (OAR) and a given number and position of needles and the position of the energy emitting source in each needle the dwell times of the energy emitting source at each position are determined, so that the resulting dose distribution satisfies various criteria such as coverage of the anatomical portion with the prescription dose, avoidance of dose values above some critical values in the specific organs, etc.

Template based Inverse Planning

Figure 6:
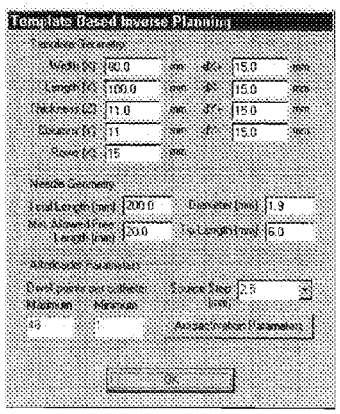
FIG. 6 shows an exemplary dialog for displaying the template and catheter characteristics.
Figure 7:
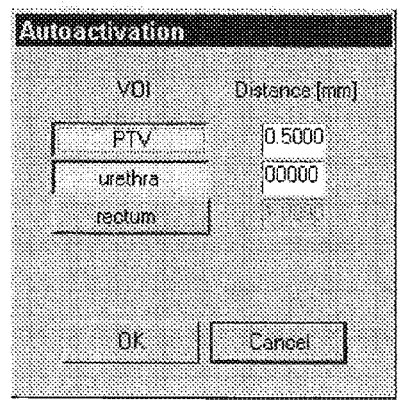
FIG. 7 shows an exemplary "auto-activation" dialog.

FIG. 6 defines the template and catheter characteristics. The planning software is run on a personal computer or laptop computer and allows the setting of certain objectives/boundaries/parameters prior to the generation of a treatment plan. The displacement step of the source within a needle is set at 5.0 mm in the afterloader parameters, since a 2.5 mm value produces a large number of sources and the optimization using the algorithm according to the invention may take more time and since then 512 MB RAM are recommended. By pressing the button Auto-activation the dialog of FIG. 7 appears, which may contain other organs (or VOIS i.e. Volumes Of Interest)

This dialog is used for the auto-activation algorithm. The anatomical organ (PTV) and the specific organs (OAR) to be protected against too much radiation exposure are listed as wels as the minimum distance of the source dwell positions from the corresponding VOI in mm. It is used to select only source dwell positions that are at a distance to a corresponding VOI larger than a specified value.

VOIs for which the corresponding button is pressed only will be considered. In this example the rectum is ignored since it is outside the anatomical portion (PTV).

Now the program moves all catheters/needles, which inside the anatomical portion taking the specific organs and the geometry of the anatomical portion into account. The user has now to take only a subset of these catheters. In principle this will be done automatically by using an optimization methods which are flexible and robust. This will be the true inverse planning.

Figure 8:
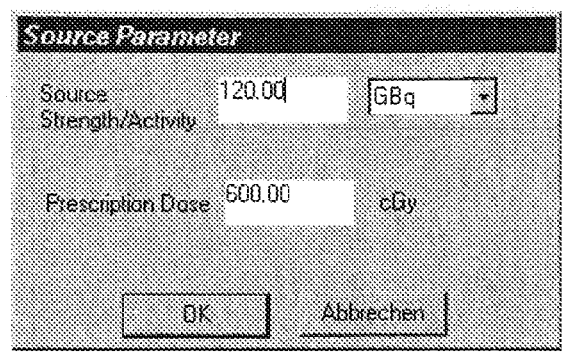
FIG. 8 shows an exemplary "source parameter" dialog.

In FIG. 8 the Source Parameter dialog for setting the prescription dose is disclosed. This dialog is used to define the source strength or activity and the prescription dose. These parameters have to be supplied for the use of the optimization algorithms. The source is characterized by its strength in units of U or as activity in units of GBq or Ci. The prescription dose is specified in cGy.

Figures 9, 10:
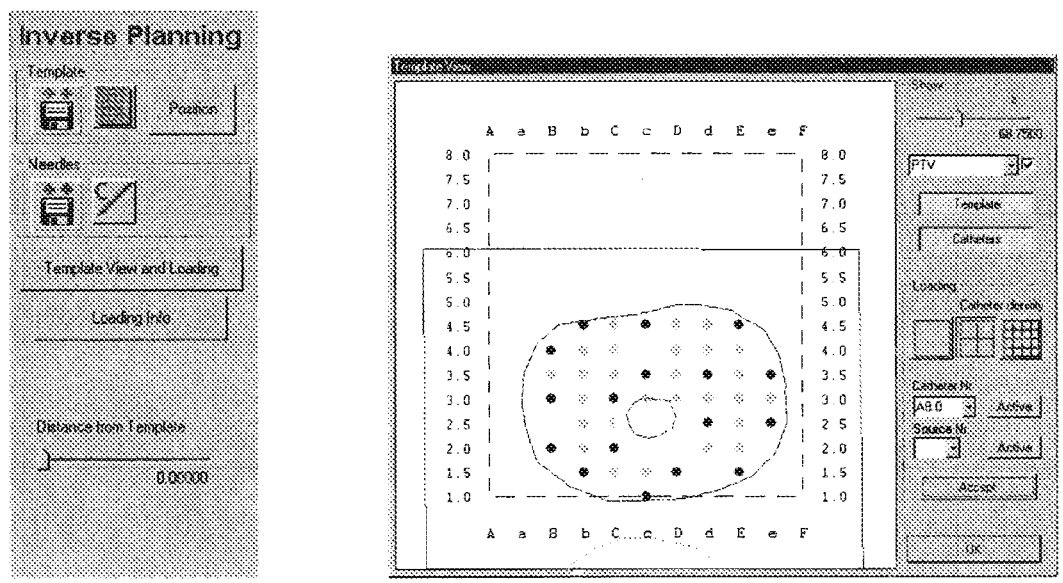
FIG. 9 shows an exemplary "inverse planning" dialog.
FIG. 10 shows an exemplary "template view and loading" dialog.

Subsequently the Inverse planning dialog of FIG. 9 and FIG. 10 Template View and Loading appears. FIG. 10 shows the grid of the template, the catheters and VOIs at various distances from the template. The selected catheters are shown in dark. The catheters which can be selected in light gray. By moving the z-slide a plane parallel is moved along the normal to the template and at some given distance from the template defined by distance z. In the Template View the intersection of the VOIs with that plane is shown in the anatomy window.

Figure 11:
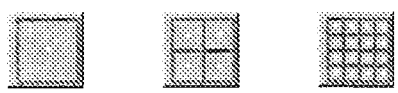
FIG. 11 shows three exemplary "loading" buttons, consistent with the embodiment of FIG. 10.

By selecting one of the buttons shown in FIG. 11 (and FIG. 10) the catheter density can be selected.

By selecting with the mouse cursor one or more of the catheters or needles (except those which are light gray) the selected catheter can be switched on or off. So the user can select the catheters he wants to use during treatment planning. For example a set of catheters on the periphery and an additional set of catheters inside the anatomical portion can be selected. It is preferred to limit the number of selected catheters or needles to 15-20 in order to limit the number of calculations to be performed.

Figure 12:
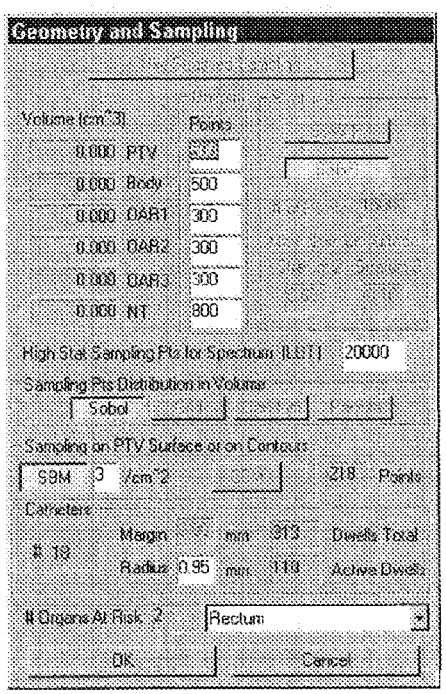
FIG. 12 shows an exemplary "geometry and sampling" dialog.

Subsequently the dialog of FIG. 12 Geometry and sampling appears which contains information about the sampling points, the number of source dwell positions and the number of catheters. Subsequently a optimization modus has to be selected and the dialog of FIG. 13 appears. Here the optimization method can be selected e.g. a deterministic optimization method.

Figure 13:
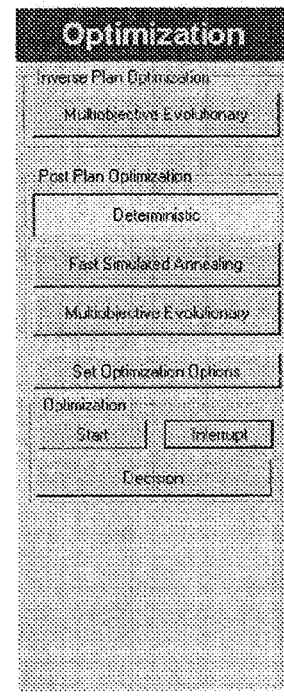
FIG. 13 shows an exemplary "optimization" dialog.
Figure 14:
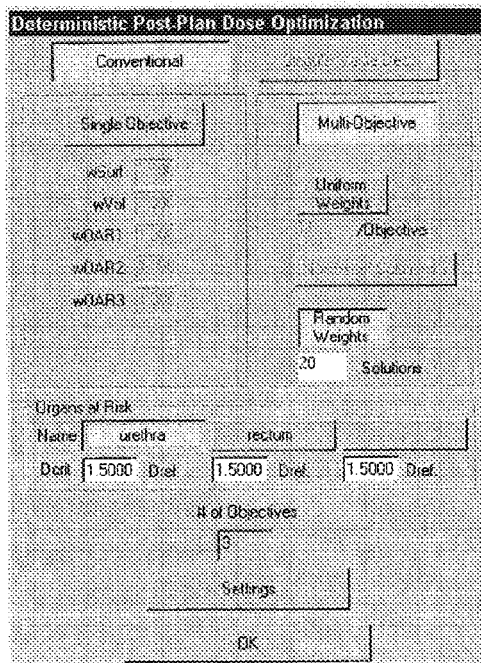
FIG. 14 shows an exemplary "post-plan dose optimization" dialog.

After selecting Set Optimization Options in FIG. 13 the dialog of FIG. 14 appears. The specific organs (OAR=Organs At Risk) which are to be considered during the radiation treatment planning have to be selected. In this case the rectum is located outside the anatomical region to be treated and it can be ignored. However in this example prostate cancer is to be treated and therefore the Urethra button is selected as the urethra is present inside the prostate. The critical dose value to which the specific organ may be exposed to as fraction of the prescription dose. In this case it is decided by the medical personnel that the urethra does not to receive more than 50% of the prescription dose. Therefore the factor 1.50 is entered.

With this dialog a single or multi-objective optimization can be performed. The multi-objective optimization is selected. After the optimization 20 solutions are presented to the user (medic personnel) of the treatment planning system. The treatment planning system Plato developed and commercialized by the present applicant Nucletron B.V. or other systems use a single set of importance factors which is not recommended because there cannot be such a single set of importance factors for all cases. There is not a single solution but in principle infinite solutions.

The treatment planning system according to the invention tries to produce a representative set of multiple treatment planning solutions. The deterministic method is the most simple approach. Recommended is of course the evolutionary algorithm which is more flexible and produces much more solutions out of which the best for each case can be found. It is not always possible to have similar results. Even if only prostate cases are considered.

After initialization the treatment planning system of the invention calculates the volumes of the anatomical portion and the specific organs, it generates the sampling points and look-up tables are filled. In this case the optimization algorithm repeats 20 times with 20 different sets of importance factors.

Figure 15:
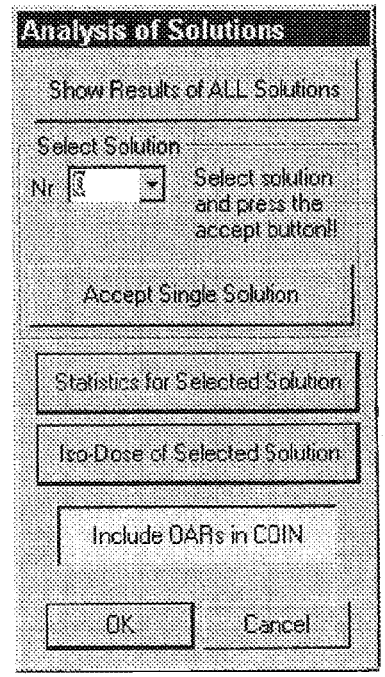
FIG. 15 shows an exemplary "analysis of solutions" dialog.

After the optimization step the Decision button has to be selected in order to select~solution and see the results. The dialog of FIG. 15 appears. When the button Show results of all solutions is pressed the dialog of FIG. 16 appears. By moving the slider to the DVH values are made visible, as these values are used in the decision making of the final treatment plan.

By selecting the column the DVH (1.500) urethra, the values in that column are sorted in descending order. See FIG. 18.

Figures 18, 19:
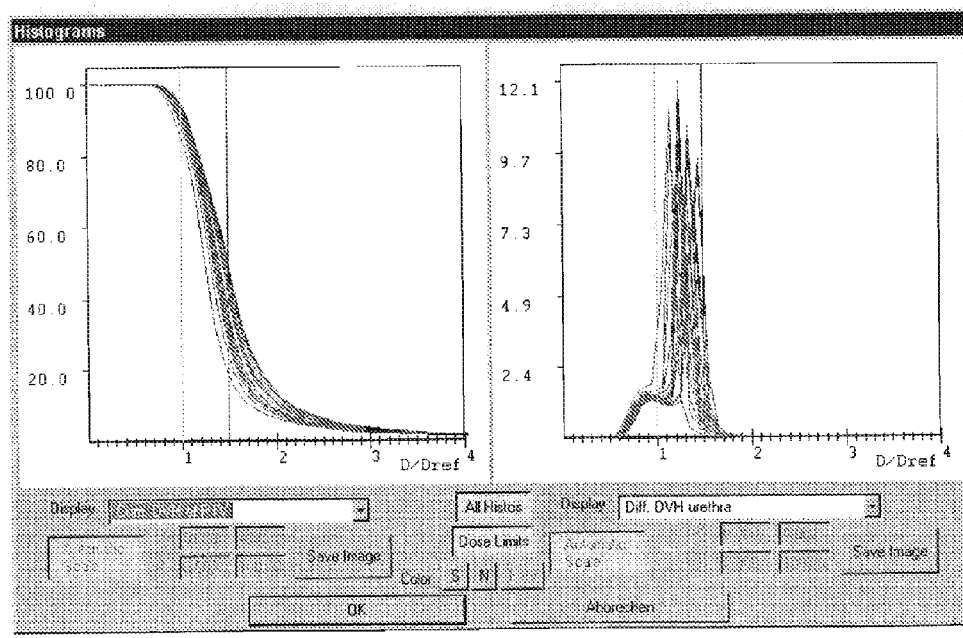
FIG. 18 shows a third exemplary view of the "show results of all solutions" dialog with values in DVH column sorted in descending order.
FIG. 19 shows exemplary histograms of radiation dose coverage of the anatomical portion (PTV)

In FIG. 18 the best radiation dose coverage of the anatomical portion (PTV) is in this example 92.13%, while 10.785% of the urethra receives a dose value above 1.5 times the prescription dose. If the medic personnel want a dose exposure of the urethra below 1% (in FIG. 18 0.77%), then the best coverage for the anatomical portion (prostate) is 86.115%. By pressing the Histogram button the distributions e.g. are displayed (FIG. 19).

The deterministic algorithms use a mean on the dose normalization for the surface of the anatomical portion and it is therefore not as flexible as the evolutionary algorithms. But the examples still show the differences between the treatment planning solutions obtained with different importance factors/boundary conditions, which can be quite large. So one method would be to consider first the specific organs (OARs), then the dose coverage of the anatomical portion (PTV) and finally the dose in the surrounding tissue. Whatever the preferences of the planner are the algorithm according to the invention generates all possible solutions and the planner can select which treatment solution is the best solution.

Figures 16, 17:
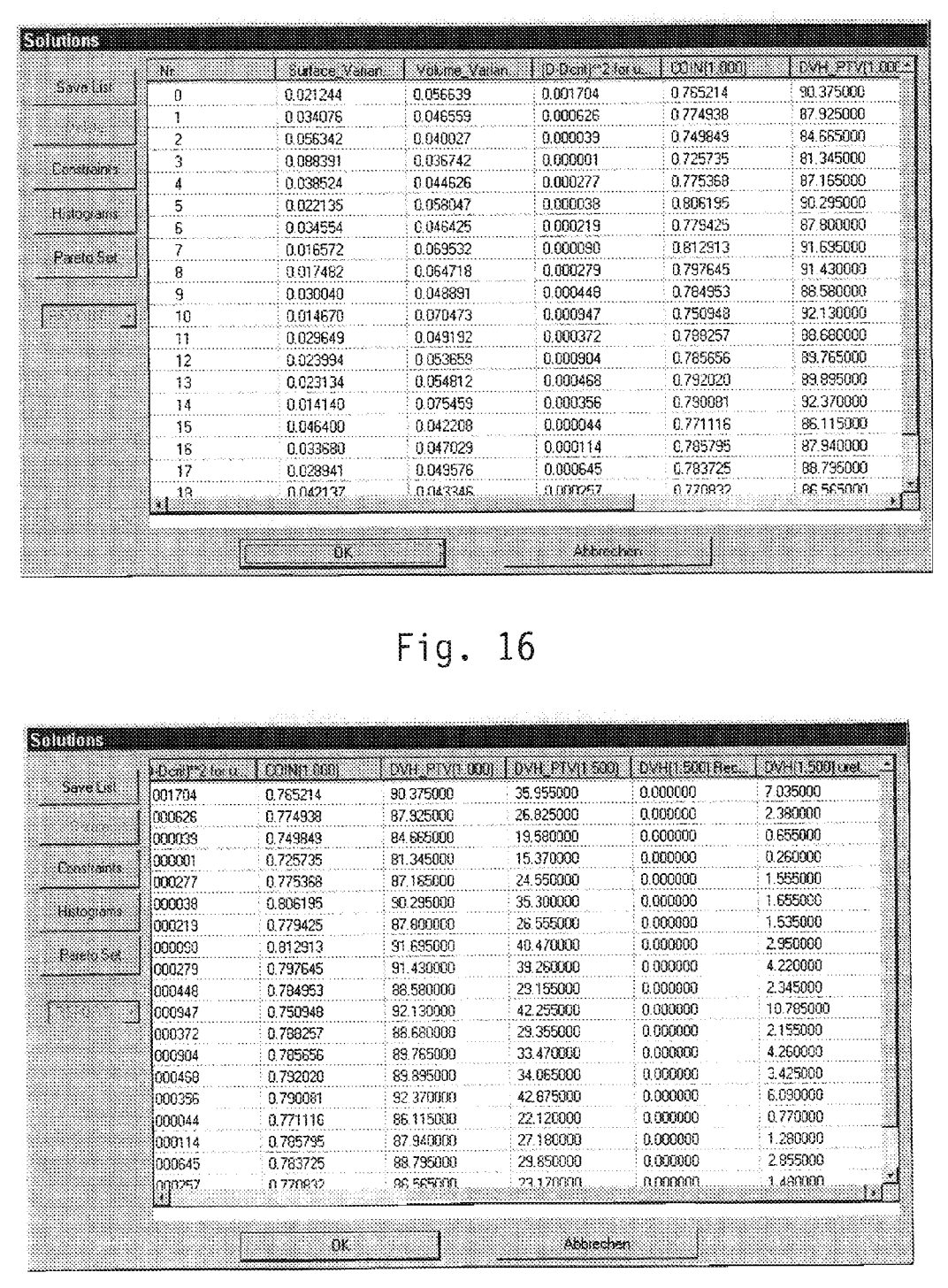
Figure 20:
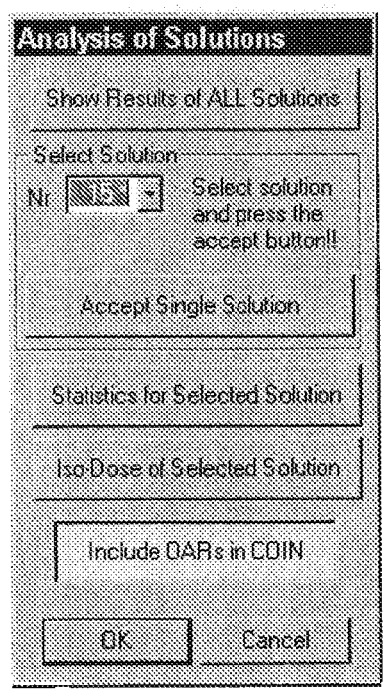
FIG. 20 shows an exemplary "analysis of solutions" dialog.

In the event that it is decided that 1% of urethra may to receive more than the critical dose value, then the treatment solution no. 15 is selected in FIG. 20 (see also FIGS. 16 and 18). When the solution 15 in the list is selected the Accept single solution button is to be pressed and for seeing the isodose distributions the Iso-Dose of Selected Solution button is to be pressed in FIG. 20.

Figure 21:
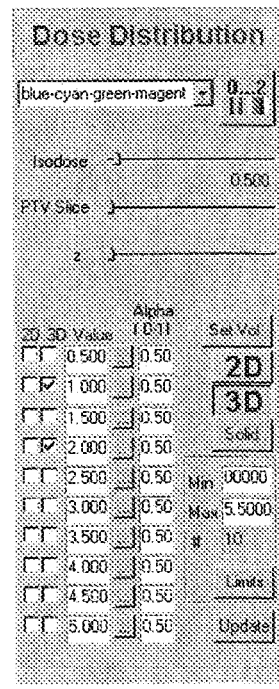
FIG. 21 shows an exemplary "dose distribution" dialog.

By selecting the 3D button in FIG. 21 the isodose values are marked, which are to be displayed (here the isodose for 1× the prescription and 2× the prescription). Subsequently two 3D isodose distributions will be displayed.

Post Implant Optimization

Figure 22:
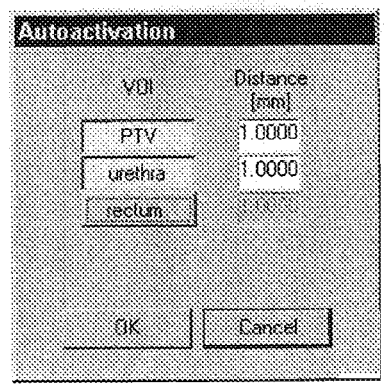
FIG. 22 shows another exemplary view of the "auto-activation" dialog.

Post Implant Optimization assumes that the source dwell positions are given. This is in principle what Nucletrons PLATO systems calls inverse planning. After activating the Post Implant Optimization the treatment planning system loads the VOIS and catheters and the Autoactivation dialog of FIG. 22 appears.

Figure 23:
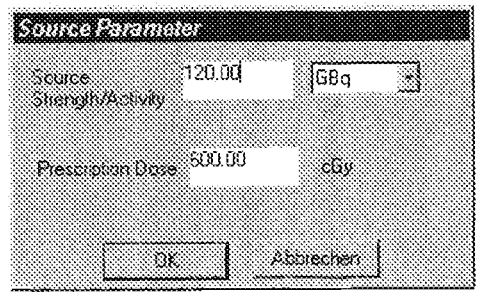
FIG. 23 shows an exemplary "source parameter" dialog.

After pressing the OK button the Source parameters dialog of FIG. 23 is displayed. After selecting the source parameters and pressing on OK the system directly continues with the optimization step of FIG. 13. Analogue to the pre-planning step the deterministic optimization algorithm can be selected. The steps of generating multiple treatment solutions are then the same as with the pre-planning step.

The invention claimed is:
1. A real-time radiation treatment planning system for use in effecting radiation therapy of a pre-selected anatomical portion of an animal body, comprising:
   an imaging device configured to generate image data corresponding to the anatomical portion;
   a radiation delivery device configured to deliver at least one energy emitting source through at least one of a plurality of hollow needles inserted into the anatomical portion;
   a processor configured to generate, in real-time, a radiation treatment plan for effecting the radiation therapy, wherein the processor is configured to:
      convert the image data into a three-dimensional image of the anatomical portion;
      designate a set of multiple sampling points in the three-dimensional image;
      calculate radiation dose distributions for the sampling points, based on at least one of an actual number and position of at least one of the hollow needles, an actual position of the at least one energy emitting source within the at least one of the hollow needles, or an actual dwell time of the at least one energy emitting source at the position;
      calculate an objective function indicative of an overall dose distribution in the anatomical portion, based on the radiation dose distributions of the sample points, wherein a number of operations for calculating the objective function is independent of the number of sampling points; and determine, based on the objective function and in real time, the radiation treatment plan reflecting a radiation dose via the at least one of the hollow needles.

2. The real-time radiation treatment planning system of claim 1, wherein the objective function is optimized using a gradient-based method.

3. The real-time radiation treatment planning system of claim 1, wherein the processor is configured to determine, in real-time, the actual number and position of at least one of the hollow needles, the actual position of the at least one energy emitting source within the at least one of the hollow needles, and the actual dwell time of the at least one energy emitting source at the position, based on the three-dimensional image and using an image segmentation algorithm.

4. The real-time radiation treatment planning system of claim 1, wherein the processor configured to determine the radiation treatment plan determines at least one of a virtual number, a virtual position, a virtual direction, or a virtual placement of the at least one of a plurality of hollow needles.

5. The real-time radiation treatment planning system of claim 1, wherein the processor configured to determine the radiation treatment plan determines a virtual amount of radiation dose to be emitted.

6. The real-time radiation treatment planning system of claim 1 further comprises a template configured to insert at least one of the plurality of hollow needles inserted into the anatomical portion.

7. The real-time radiation treatment planning system of claim 1, wherein the template includes a grid configuration having needle holes at a substantially constant intermediate distance along a diagonal or an orthogonal direction.

8. The real-time radiation treatment planning system of claim 1, wherein the template includes a guiding tube for guiding the plurality of hollow needles, wherein the guiding tube is configured to be positioned as generated in the treatment plan.

9. The real-time radiation treatment planning system of claim 1, wherein the processor is further configured to calculate a gradient function of the objective function, wherein a number of operations for calculating the gradient function is independent of the number of sampling points.

10. The real-time radiation treatment planning system of claim 9, wherein the processor is configured to adjust the radiation treatment plan based on the gradient function of the objective function, such that the adjusted radiation treatment plan yields an updated value of the objective function smaller than a previous value.

11. The real-time radiation treatment planning system of claim 1, wherein the sampling points are generated using a quasi-random number generator.

12. The real-time radiation treatment planning system of claim 4, wherein the processor is further configured to:
display the virtual position of each of the plurality of hollow needles as determined in the treatment plan in the three-dimensional image of the anatomical portion on a screen; and
guide the at least one of the plurality of hollow needles into the anatomical portion and to the virtual position.

13. A method for generating a radiation treatment plan for use in effecting radiation therapy of a selected anatomical portion of an animal body of a patient, comprising the steps of:
generating image data corresponding to the anatomical portion;
inserting at least one of a plurality of hollow needles into the anatomical portion;
converting the image data into a three-dimensional image of the anatomical portion;
designating a set of multiple sampling points in the three-dimensional image;
calculating radiation dose distributions for the sampling points, based on at least one of an actual number and position of at least one of the hollow needles, an actual position of the at least one energy emitting source within the at least one of the hollow needles, or an actual dwell time of the at least one energy emitting source at the position;
calculate an objective function indicative of an overall dose distribution in the anatomical portion, based on the radiation dose distributions, wherein a number of operations for calculating the objective function is independent of the number of sampling points; and
determining, based on the objective function and in real time, a radiation treatment plan reflecting a radiation dose via the at least one of the hollow needles.

14. The method of claim 13, wherein the objective function is optimized using a gradient-based method.

15. The method of claim 13 further comprises determining, in real-time, the actual number and position of at least one of the hollow needles, the actual position of the at least one energy emitting source within the at least one of the hollow needles, and the actual dwell time of the at least one energy emitting source at the position, based on the three-dimensional image, or using an image segmentation algorithm.

16. The method of claim 13, wherein determining the radiation treatment plan comprises determining at least one of a virtual number, a virtual position, a virtual direction, or a virtual placement of the at least one of a plurality of hollow needles.

17. The method of claim 13, wherein determining the radiation treatment plan comprises determining a virtual amount of radiation dose to be emitted.

18. The method of claim 13 further comprises calculating a gradient function of the objective function, wherein a number of operations for calculating the gradient function is independent of the number of sampling points.

19. The method of claim 18 further comprises adjusting the radiation treatment plan based on the gradient function, such that the adjusted radiation treatment plan yields an updated value of the objective function smaller than a previous value.

20. The method of claim 13 further comprises:
displaying the virtual position of each of the plurality of hollow needles as determined in the treatment plan in the three-dimensional image of the anatomical portion on a screen; and
guiding the at least one of the plurality of hollow needles into the anatomical portion and to the virtual position.

* * * * *